United States Patent
Helasuo et al.

(10) Patent No.: US 7,762,123 B2
(45) Date of Patent: Jul. 27, 2010

(54) SEAL FOR MEASURING DEVICE

(75) Inventors: Jarmo Helasuo, Espoo (FI); Olli Ruosaari, Tampere (FI); Kari Laukkanen, Espoo (FI)

(73) Assignee: Metso Automation Oy, Helsinki (FI)

( * ) Notice: Subject to any disclaimer, the term of this patent is extended or adjusted under 35 U.S.C. 154(b) by 689 days.

(21) Appl. No.: 10/582,738

(22) PCT Filed: Dec. 13, 2004

(86) PCT No.: PCT/FI2004/000758

§ 371 (c)(1),
(2), (4) Date: Jul. 6, 2007

(87) PCT Pub. No.: WO2005/057059

PCT Pub. Date: Jun. 23, 2005

(65) Prior Publication Data

US 2008/0246230 A1    Oct. 9, 2008

(30) Foreign Application Priority Data

Dec. 15, 2003    (FI) ................................. 20031829

(51) Int. Cl.
G01N 11/14    (2006.01)
(52) U.S. Cl. ....................... 73/54.28; 74/54.23; 285/227
(58) Field of Classification Search ................ 73/54.23, 73/54.28
See application file for complete search history.

(56) References Cited

U.S. PATENT DOCUMENTS

| 3,181,349 | A | 5/1965 | Jansson |
| 4,345,772 | A | 8/1982 | Woody et al. |
| 4,653,313 | A | 3/1987 | Sabins et al. |
| 4,823,594 | A | 4/1989 | Gray |
| 5,176,576 | A | 1/1993 | Moulindt |
| 6,151,957 | A | 11/2000 | Enarson |
| 6,315,332 | B1 * | 11/2001 | Aschoff et al. ............. 285/227 |
| 2004/0004702 | A1 * | 1/2004 | Phillips et al. ................ 355/53 |

FOREIGN PATENT DOCUMENTS

| EP | 0 736 679 A1 | 10/1996 |
| GB | 2 184 811 A | 7/1987 |
| WO | WO 91/14168 A1 | 9/1991 |

\* cited by examiner

*Primary Examiner*—Hezron Williams
*Assistant Examiner*—Mark Shabman
(74) *Attorney, Agent, or Firm*—Alston & Bird LLP

(57) ABSTRACT

The invention relates to a seal intended for sealing an axis pair, whereby the axes rotate in the same direction, the inner one of the axes is inside the outer axis and the phase difference of the axes is arranged to remain within predefined limits. The seal (200) is a tubular seal made of an elastic material and comprises at least two tube sections (202, 204) fixed to each other. Folds (212, 214) of the at least two tube sections (202, 204) have opposing twisting angles. One end of the seal (200) is fastened to the outer axis and the other end is fastened to the inner axis, and the seal (200) is arranged to twist by a torque proportional to the phase difference between the axes.

17 Claims, 5 Drawing Sheets

SEAL FOR MEASURING DEVICE

FIELD

Figure 1:
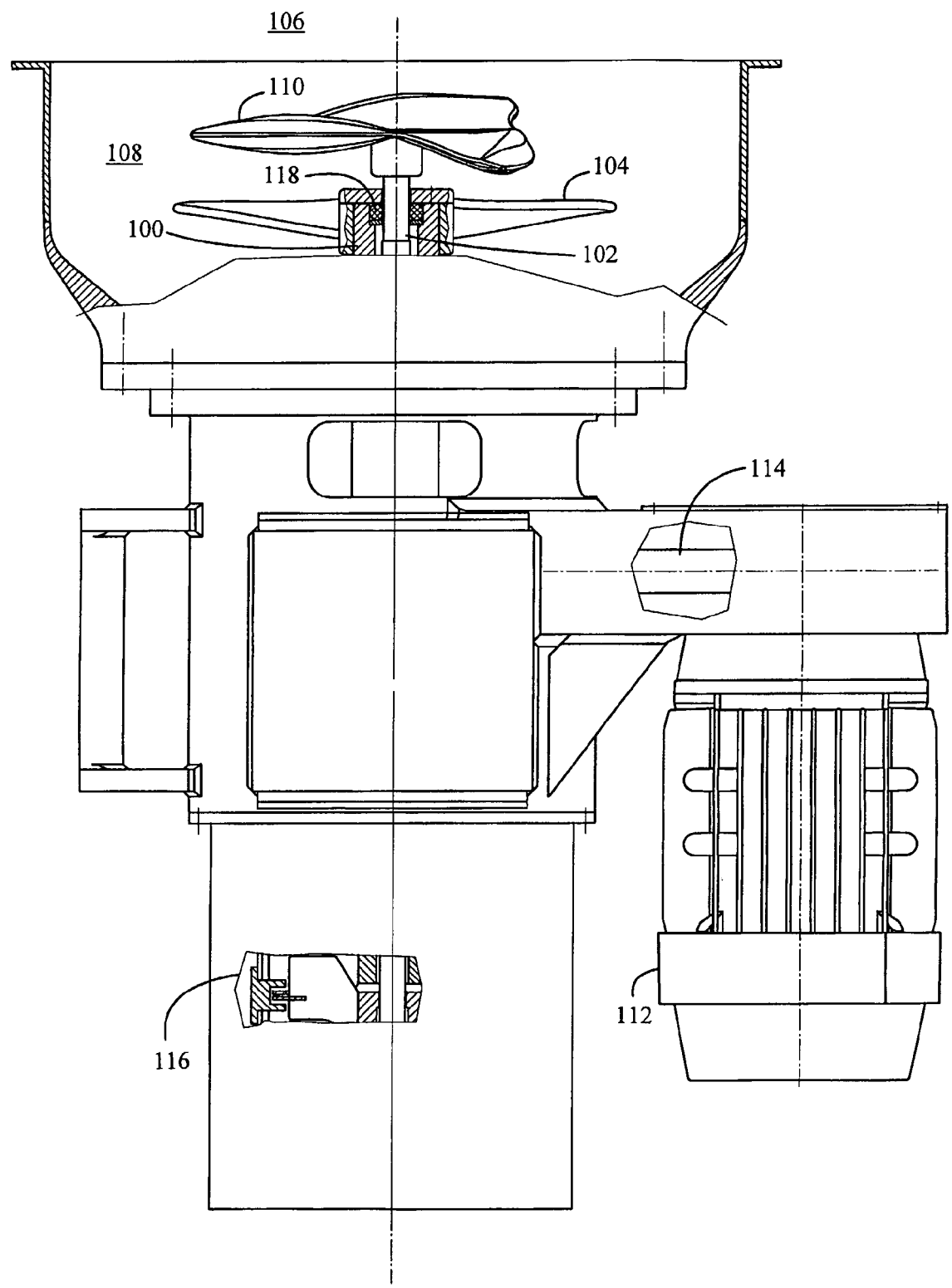

The invention relates to a seal, measuring device, measuring method and seal manufacturing method in association with a fluid measurement performed by a biaxial measuring device.

BACKGROUND

Pulp consistency, for instance, is measured in the processing industry by using a biaxial measuring device where the axes are within each other. The axes are pivoted elastically to each other, enabling a limited twisting between the axes. The twisting, which can also be expressed as a phase difference, can be few degrees at the maximum.

The axes affect each other by means of magnetic fields produced by electromagnets, and thus, when the first axis is rotated, for instance, by an electromotor in the pulp to be measured, the other axis rotates as well. At the ends of the axes there are different protrusions, the rotation of which the pulp to be measured tries to decelerate to the different extents by its consistency. This causes a torque between the axes, tending to increase the phase difference between the axes pivoted elastically. The aim is, however, to keep the phase difference constant during the measurement by controlling the amount of current to be supplied to the coils, whereupon alternating magnetic forces compensate for the torque between the axes accurately. Pulp consistency, which is proportional to the torque, can be determined by measuring the current supplied to the coils. Generally, shearing and friction forces, viscosity or consistency of fluids can be measured correspondingly.

In the prior art, the gap between the axes is sealed with an elastomer seal, such as an O-ring seal. The use of the O-ring is, however, related with problems. Especially when the phase difference of the axes increases and varies, the O-ring slides, which changes the friction between the axes in a non-predefined way. In addition, since the seal has to withstand temperature variations and possibly various chemicals in the process, the properties of the elastomer seal change in the course of time, which also changes the friction between the axes in an unknown manner. Since the friction between the axes, consisting of the friction between the seal and the axes and the friction inside the seal, affects the torque between the axes, occasional and/or non-predefined changes caused by the seal in the torque hinder the measurement of fluid properties considerably. If this affects the process control, the entire process to be controlled might be brought into a false state and the quality of the end product becomes poorer.

BRIEF DESCRIPTION

It is an object of the invention to provide an improved seal, measuring device, seal manufacturing method and measuring method. This is achieved by a seal intended for sealing an axis pair in connection with a fluid measurement, whereby the axes rotate in the same direction, the inner one of the axes is inside the outer axis and the phase difference of the axes is arranged to remain within predefined limits. Furthermore, the seal is a tubular seal made of an elastic material; the seal comprises at least two tube sections fixed to each other; folds of the at least two tube sections have opposing twisting angles; one end of the seal is fastened to the outer axis and the other end is fastened to the inner axis; and the seal is arranged to twist by a torque proportional to the phase difference between the axes.

The invention also relates to a measuring device comprising an axis pair rotating in the same direction, the inner axis being inside the outer axis; the measuring device comprises a seal intended for sealing the axis pair; the measuring device is arranged to determine a property of a fluid to be measured when the fluid causes a phase difference between the axes by the torque it has produced. Further, the seal is a tubular seal made of an elastic material; the seal comprises at least two tube sections fixed to each other; folds of the at least two tube sections have opposing twisting angles; one end of the seal is fastened to the outer axis and the other end is fastened to the inner axis; and the seal is arranged to twist by a torque proportional to the phase difference between the axes.

The invention further relates to a measuring method, wherein a property of a fluid is measured on the basis of a phase difference between two axes within each other and rotating in the same direction, the phase difference being produced by the torque between the axes the fluid has caused. The method further comprises producing by means of a seal, which is a tubular seal made of an elastic material and comprising at least two tube sections fixed to each other, a torque twisting in the opposite direction than the torque caused by the fluid between the axes and being proportional to the phase difference between the axes; each tube section comprises at least one fold; the folds of the at least two tube sections have opposing twisting angles; one end of the seal is fastened to the outer axis and the other end is fastened to the inner axis; the phase difference between the axes is measured; and the fluid property is determined on the basis of the phase difference.

The invention also relates to a seal manufacturing method, wherein the seal is intended for sealing an axis pair of a measuring device, whereby the axes rotate in the same direction, the inner one of the axes is inside the outer axis and the phase difference of the axes is arranged to remain within predetermined limits. The method further comprises making a tubular seal of an elastic material; providing the seal with at least two tube sections; providing each tube section with at least one fold, the twisting angle of which differs from the direction of the longitudinal axis of the tubular seal; providing the at least two tube sections with folds having opposing twisting angles to make the torque caused by the twisting of the seal during the measurement proportional to the phase difference between the axes; providing the seal ends with fastening parts, by which the seal can be fastened to the axis pairs in such a manner that one end of the seal is fastened to the outer axis and the other end is fastened to the inner axis.

Preferred embodiments of the invention are described in the dependent claims.

The method and system of the invention provide several advantages. The properties of the seal remain unchanged with respect to time. The seal does not cause non-predefined changes in the torque between the axes in different process conditions, which makes the measurement more accurate.

LIST OF FIGURES

Figure 2:
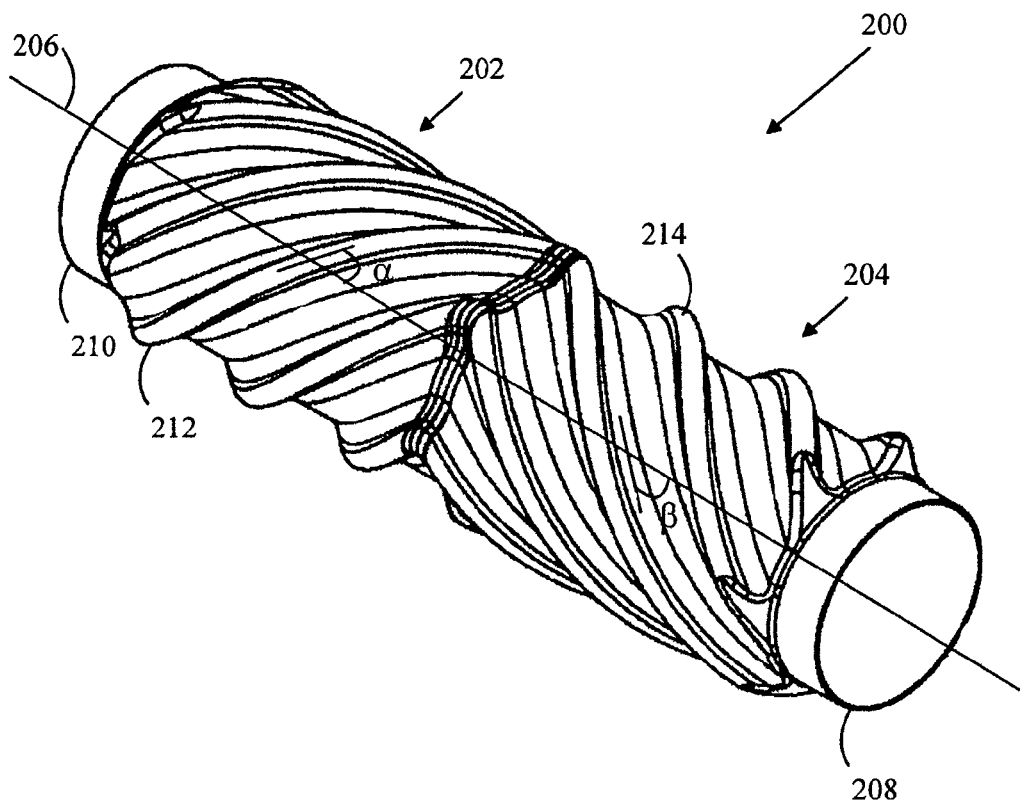
Figure 3:
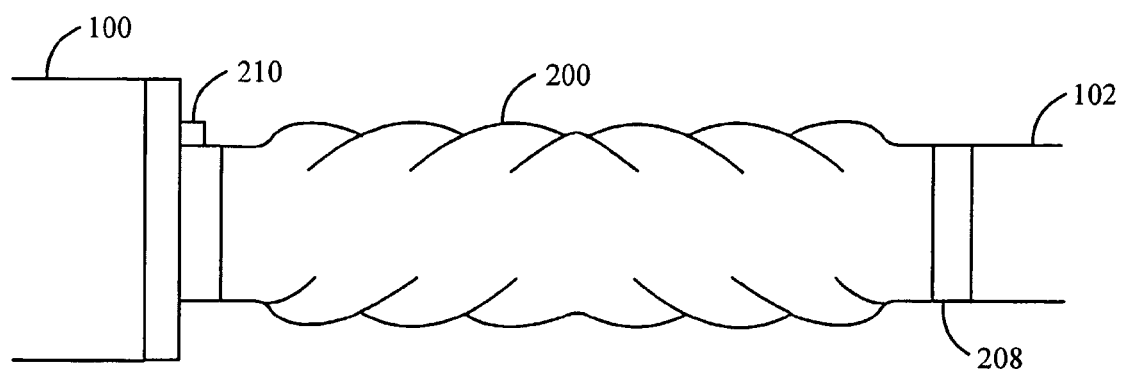
Figure 4A:
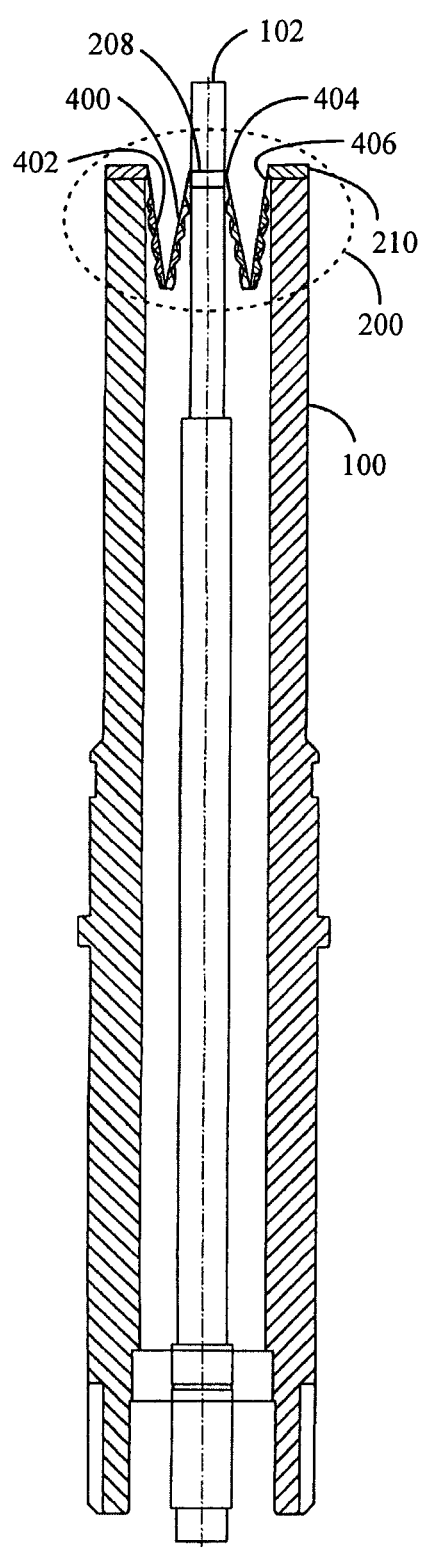
Figure 4B:
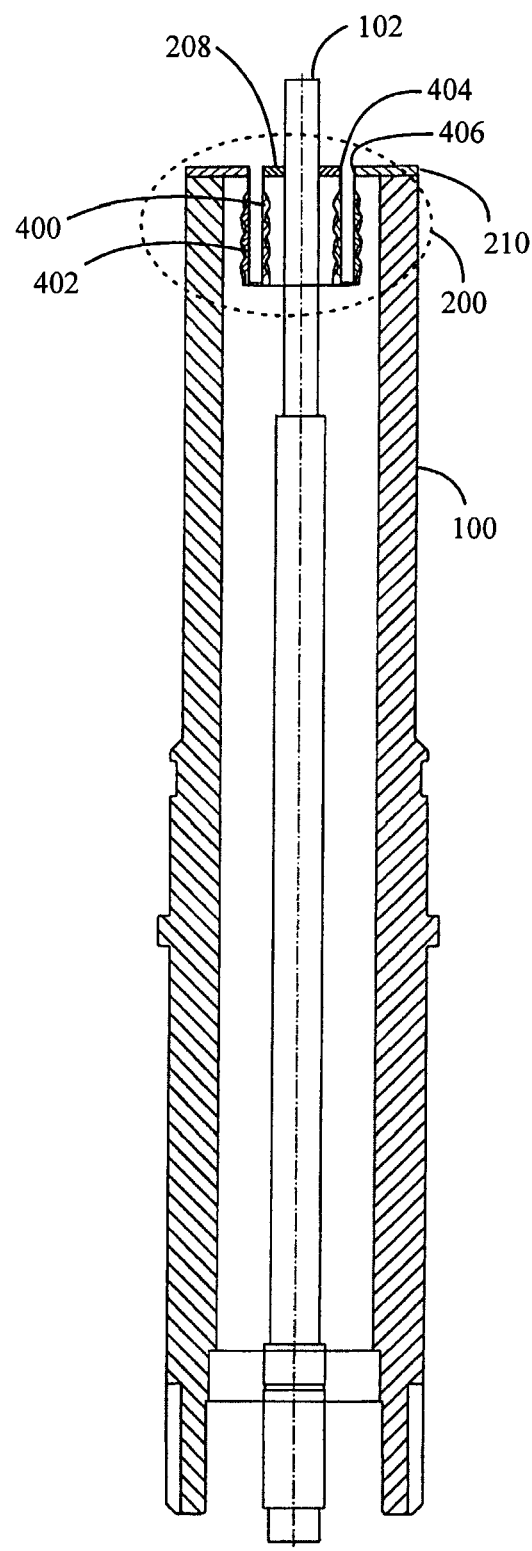
Figure 5:
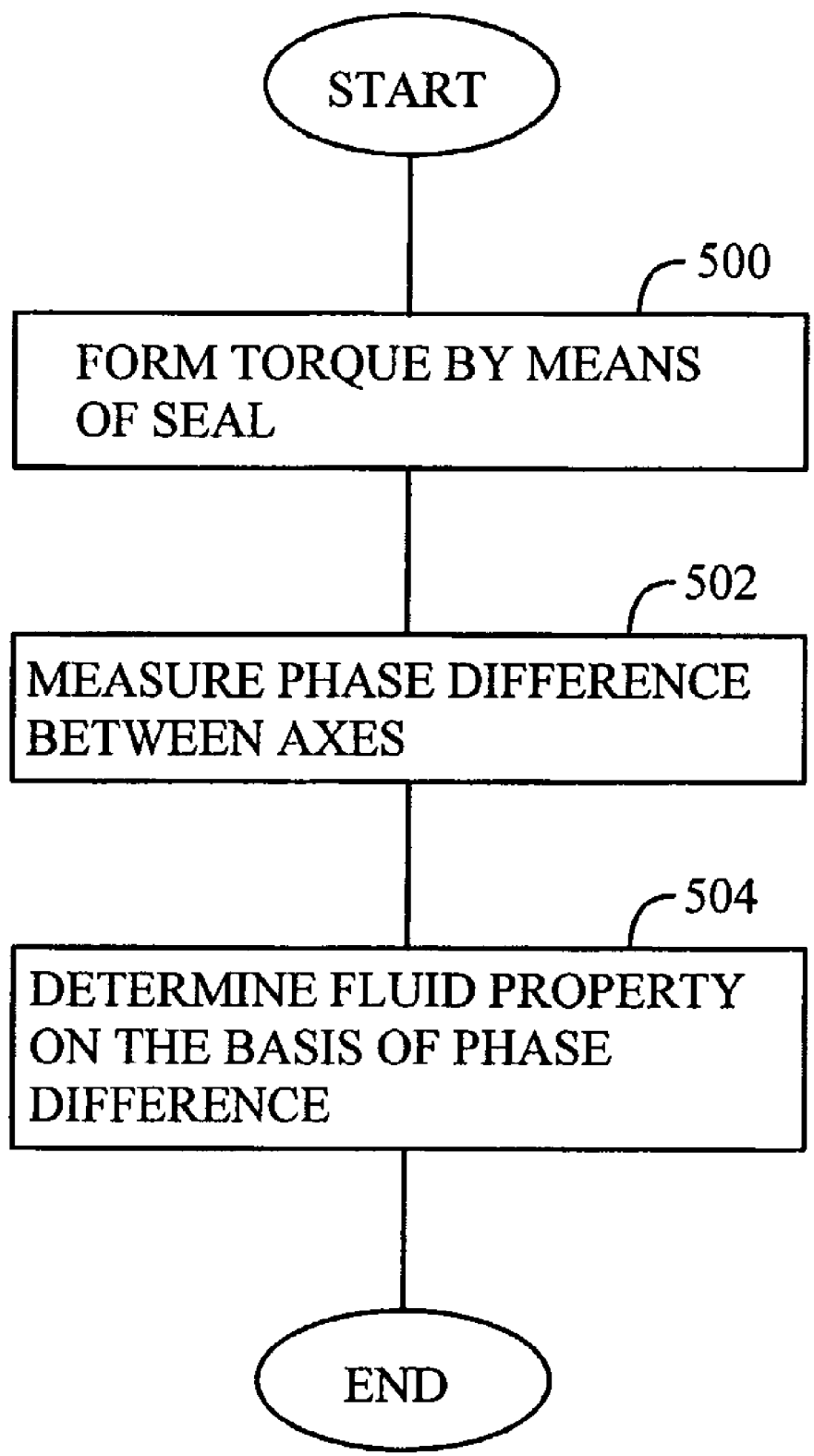
Figure 6:
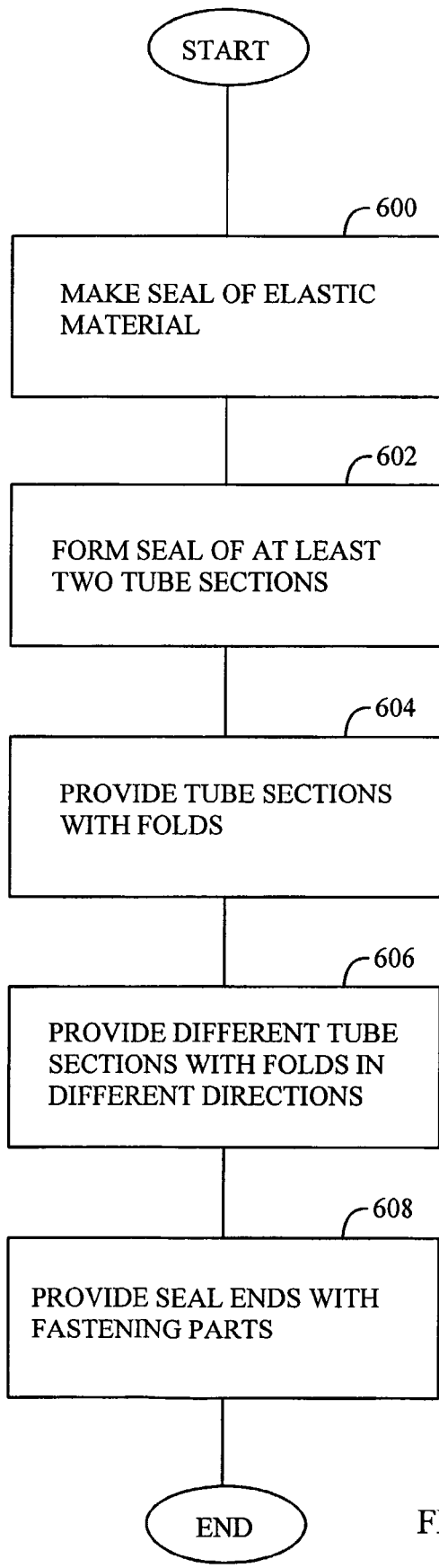

The invention will now be described in closer detail in association with the preferred embodiments, in which FIG. 1 shows a device for measuring consistency, FIG. 2 shows a seal, FIG. 3 shows a seal fastened to axes, FIG. 4A shows a seal with tube sections within each other, FIG. 4B shows a seal with tube sections within each other, FIG. 5 shows a flow chart of a measuring method, and FIG. 6 shows a flow chart of a manufacturing method.

DESCRIPTION OF EMBODIMENTS

The shown solution is suitable for measuring consistency, viscosity, shearing and friction forces of a fluid. The solution can be applied, for instance, in paper, paperboard and pulp industries and in waste water treatment without, however, restricting thereto. The fluid to be measured can be a liquid, gas or suspension.

FIG. 1 shows a biaxial measuring device, by which, for instance, consistency of a suspension comprising wood fibre can be measured, for which purpose the shown solution is very well suitable. The solution comprises two axes so that inside an outer axis 100 there is an inner axis 102. At the end of the outer axis 100 there may be a propeller 104, which, during its rotation, can draw fluid to be measured on the main flow of a process tube 106 to a measuring chamber 108. The propeller 104 can also mix the suspension during the measurement. At the end of the inner axis 102 there can be a sensor 110. An electromotor 112 or the like can rotate the axis 100 by means of a belt drive 114, for instance, with a constant speed or in another known way. Both axes rotate in the same direction, and by means of an electromagnetic connection between the axes in a measuring part 116, the axes 100, 102 are kept in a constant phase with respect to each other, although the shearing and friction forces of the fluid to be measured tend to change the phase difference by means of the torque they have produced between the axes.

A phase difference between the axes refers to a twist between the axes with regard to a predefined initial position. The axes which are usually pivoted elastically to each other can twist few degrees at the maximum. The phase difference can be measured optically by using, for instance, an optical measuring device in the measuring part 116 comprising an optical transmitter, optical receiver and two similar cogwheels (not shown in FIG. 1). The first cogwheel is rotated by the outer axis 100 and the second cogwheel is rotated by the inner axis 102. As the cogwheels rotate together with the axes, the teeth act as a chopper of the beam between the optical transmitter and receiver and form a pulsed signal for the receiver. When the axes 100, 102 are cophasal, the teeth of the cogwheels can be aligned with each other. But when there is phase difference between the axes 100, 102, the teeth of the cogwheels are displaced correspondingly with respect to each other. This changes the impulse ratio of the optical signal. The phase difference is thus directly proportional to the impulse ratio. The phase difference can also be measured with other manners known per se.

In the prior art, between the axes 100, 102 there is an O-ring 118, which is problematic, as was described above.

FIG. 2 shows a seal replacing the O-ring 118. A tubular seal 200, which is made of a continuous material and resembles a bellows seal, comprises two tube sections 202, 204 fixed to each other. Tubularity means that the cross-sectional profile of the seal forms a closed circumference, which can have a shape of a circumference of e.g. a circle, ellipse, polygon or any other figure drawn with a continuous curve. Usually there can be more than two tube sections. The tube sections 202, 204 of the seal 200 can be in successive order, whereby each tube section 202, 204 increases the length of the seal 200 by its own length. The tube section 202 of FIG. 2 may comprise 6 wavelike folds 212. The tube section 204 may also comprise 6 wavelike folds 214. Each tube section can have a desired number of folds so that usually each tube section comprises at least one fold. The twisting angle of the folds 212 of the tube section 202 with respect to the longitudinal axis 206 of the seal is $\alpha$. The twisting angle of the folds 214 of the tube section 202 with respect to the longitudinal axis 206 of the seal is $\beta$. The number of folds of the two different tube sections of the seal 200 can differ from each other. In FIG. 2, the folds of the tube sections 200, 202 of the seal 200 twist in the different directions. Generally the folds of the at least two different tube sections in the seal 200 have opposing twisting angles. The twisting angles of the folds relating to the twisting of the tube sections differ from the direction of the longitudinal axis 206 of the tubular seal and from the direction which is at an angle of 90° with respect to the direction of the longitudinal axis 206 of the seal. Thus, if the twisting angle of the tube section 202 is $\alpha=45°$ from the direction of the longitudinal axis 206 of the tubular seal, the twisting angle of the tube section 204 can be $\beta=-45°$ from the direction of the longitudinal axis 206 of the tubular seal, wherein the minus sign refers to the opposite twisting angle. On the other hand, the twisting angle of the tube section 204 can also be $\beta=-30°$ from the direction of the longitudinal axis 206 of the tubular seal, because the absolute value of the twisting of the folds need not be equally high in the different tube sections. At its both ends, the seal can comprise fastening parts 208, 210 for fastening the seal to the axes. The opposite twisting angles of the folds enable that the ends of the seal do not twist if compression occurs in the direction of the longitudinal axis 206.

FIG. 3 shows a seal in its place between the axes. A tubular seal 200 is fastened at its one end to the inner axis 102 by using a fastening part 208 and the seal 200 is fastened at its other end to the outer axis 100 by using a fastening part 210.

FIG. 4A shows a solution where at least one tube section 400 of the tubular seal is inside at least one other tube section 402 so that an end 404 of the tube section 400 that is inside and forms one end of the seal can be fastened to the inner axis by means of the fastening part 208 and the other end 406 of the seal can be fastened to the outer axis by means of the fastening part 210.

FIG. 4B also shows a solution where at least one tube section 400 of the tubular seal is inside at least one other tube section 402 so that the end 404 of the tube section 400 that is inside and forms one end of the seal can be fastened to the inner axis by means of the fastening part 208 and the other end 406 of the seal can be fastened to the outer axis by means of the fastening part 210. Unlike in the solution of FIG. 4A, the tube sections in FIG. 4B are parallel and not at an oblique angle to each other.

The seal is made of an elastic material, e.g. metals and metal alloys. An elastic object returns to its former shape when the force causing the deformation no longer affects. This is why the elastic object does not have a permanent deformation. An elastic material can be linearly or non-linearly elastic. Stainless steel, for example, is a suitable manufacturing material for a seal, because a seal made thereof withstands various kinds of process conditions. Elasticity of the material guarantees that the compression against the seal in the direction of the longitudinal axis 206 or the twisting in the circumferential direction is reversible after the force causing the compression or twisting no longer has an effect. Due to the elasticity, the seal 200 also produces between the axes twisting with respect to each other a torque $\tau$, which is proportional to the phase difference between the axes, i.e. the angle $\theta$ between the twisted axes:

$$\tau = f(\theta), \tag{1}$$

where f is a function, by which the torque depends on the phase difference. The torque can be linearly proportional to the phase difference between the axes, whereby it can be written:

$$\tau = k\theta, \quad (2)$$

where k is a torsion spring constant, which depends, like the function f, at least on material (elasticity modulus of the material), material thickness, cross-profile dimensions of a tubular seal, length of the seal and the tube sections, number and shape of folds. (1 Nm)/(1°), for instance, can be selected as the value for the constant k. The desired value for the constant k is obtained by making the seal of a desired material with suitable measures. The properties of the seal remain unchanged also in long-term use. Compared to the torque caused by the fluid, the absolute value of the torque $\tau$ of the seal is of the same magnitude but has the opposite direction. When the seal is used, an electromagnetic coupling between the axes is not necessarily required, since a fluid property can be determined directly on the basis of the phase difference between the axes. A fluid property, such as consistency c, can be determined empirically on the basis of the torque.

The entire seal can be made of the same material, where the material thickness remains constant, and the different tube sections can have the same measures with the same height and number of folds. The absolute values of the twisting angles of the folds can also be the same. However, the materials of the at least two tube sections can also differ from each other in the shown solution. In this case, the different tube sections are manufactured separately and are then fixed to each other. Since the compression in the longitudinal direction of the seal must not cause twisting of the seal or a phase difference between the axes, the effect of the different elasticity moduli of different materials should be compensated for. This is possible, for example, by manufacturing the different tube sections so that they have different lengths. Since the elasticity modulus of steel, for instance, is about three times higher than that of aluminium, the tube section made of steel should be about three times longer than the tube section made of aluminium. Correspondingly, instead of the length, it is possible to change the thickness of the wall, height of the folds, number of folds or a combination of said properties.

In the shown solution, the thicknesses of the wall of the at least two tube sections or the heights of the folds and the number of folds can also differ from each other. Each of these differences of the tube sections can be compensated for by one or more other differences between the tube sections, as was described in association with the difference between the materials. Adding more folds or increasing the height of the folds weakens the torsional rigidity of the seal, which means that the torsion spring constant k decreases. When the absolute value of the twisting angle of the folds is $|\alpha|=|\beta|=45°$, the torsional rigidity of the seal is at its minimum. Decreasing or increasing the twisting angle with respect to this value causes that the torsional rigidity of the seal increases. And, if the average diameter of the tubular seal becomes smaller, the torsional rigidity decreases. When the length measures of the seal are changed, the torsional rigidity can usually be assumed to be at least approximately linear. The exact torsional rigidity of the seal can be measured before taking it into use.

When the tubular seal comprises at least two tube sections with opposite twisting angles of the folds, the compression against the seal in the direction of the longitudinal axis 206 does not cause a phase difference between the axes, i.e. the ends of the seal do not twist with respect to each other. Compression can be caused by a process pressure, for instance, which can be dozens of bars in the paper industry.

Let us examine a flow chart of the measuring method by means of FIG. 5, where a property of the fluid is measured on the basis of the phase difference between two rotating axes 100, 102 within each other in the measuring device, whereby the fluid causes the torque between the axes. In step 500, the seal 200, which is a tubular seal made of an elastic material and comprises at least two tube sections fixed to each other, produces a torque which twists in the opposite direction than the torque caused by the fluid and is linearly proportional to the phase difference between the axes. Each tube section comprises at least one fold. The folds of the at least two tube sections have opposing twisting angles with respect to the longitudinal axis of the seal. One end of the seal is fastened to the outer axis and the other end is fastened to the inner axis. In step 502, the phase difference between the axes is measured and in step 504 the fluid property is determined on the basis of the phase difference.

Let us still examine a seal manufacturing method by means of FIG. 6, the seal being intended for sealing the axis pair 100, 102 of the measuring device, whereby the axes rotate in the same direction, the inner one of the axes is inside the outer axis and the phase difference of the axes is arranged to remain within predefined limits. In step 600, a tubular seal 200 is made of an elastic material. In step 602, a seal is formed of at least two tube sections 202, 204, 400, 402. In step 604, each tube section is provided with at least one fold, the twisting angle of which differs from the direction of the longitudinal axis of the tubular seal. In step 606, the at least two tube sections are provided with folds, which have opposing twisting angles, in order to make the torque caused by the twisting of the seal during the measurement proportional to the phase difference between the axes. In step 608, the ends of the seal are provided with fastening parts 208, 210, by which the seal can be fastened to the axis pairs in such a manner that one end of the seal is fastened to the outer axis and the other end is fastened to the inner axis.

Folds 212, 214 can have a desired shape and size, they can be e.g. wavelike embossings or grooves in the tubular structure of the seal. Due to the folds, the wall of the seal can be thicker than the wall of a non-folded wall and yet the same torsional rigidity is achieved. A seal with a thick wall withstands greater process pressures than a seal with a thin wall.

The seal can be manufactured by welding, roll forming or by hydroforming. In fluid pressure forming, inside a tube billet sealed at its ends a pressure high enough to swell the tube billet is produced. A mould surrounds the outer surface of the tube billet, and the tube billet swells to have the shape of the mould. The shown seal can have many different sizes and various materials can be used as the manufacturing material. The seal can have, for instance, the following measures: length 100 mm, diameter 14 mm, wall thickness 0.2 mm, number of folds 9 and height of folds 1 mm. These measures can produce a torsion spring constant of about 1 Nm/1°.

Although the invention is described above with reference to the examples according to the attached drawings, it is obvious that the invention is not restricted thereto, but it can be varied in many ways within the scope of the attached claims.

The invention claimed is:

1. A seal intended for sealing an axis pair in connection with a fluid measurement, the axis pair including an outer element coaxially arranged with and configured to surround an inner element, with the inner and outer elements being configured to share a common axis, whereby the inner and outer elements rotate in the same direction, and a phase difference between the inner and outer elements is arranged to remain within predefined limits, wherein
- the seal is a tubular seal made of an elastic material;
- the seal comprises at least two tube sections fixed to each other;
- folds of the at least two tube sections have opposing twisting angles;
- one end of the seal is fastened to the outer element and the other end is fastened to the inner element; and
- the seal is arranged to twist by a torque proportional to the phase difference between the inner and outer elements.

2. A seal as claimed in claim 1, wherein at least one tube section of the seal is inside at least one other tube section so that the tube section which is inside and the end of which forms one end of the seal can be fastened to the inner element and the other end of the seal can be fastened to the outer element.

3. A seal as claimed in claim 1, wherein the tube sections of the seal are in successive order, whereby each tube section increases the length of the seal by its own length.

4. A seal as claimed in claim 1, wherein the materials of the at least two tube sections differ from each other.

5. A seal as claimed in claim 1, wherein the wall thicknesses of the at least two tube sections differ from each other.

6. A seal as claimed in claim 1, wherein the lengths of the at least two tube sections differ from each other.

7. A seal as claimed in claim 1, wherein the heights of the folds of the at least two tube sections differ from each other.

8. A seal as claimed in claim 1, wherein the numbers of folds of the at least two tube sections differ from each other.

9. A measuring device comprising an axis pair rotating in the same direction, the axis pair including an outer element coaxially arranged with and configured to surround an inner element, with the inner and outer elements being configured to share a common axis;
- the measuring device comprises a seal intended for sealing the inner and outer elements;
- the measuring device is arranged to determine a property of a fluid to be measured when the fluid causes a phase difference between the inner and outer elements by the torque it has produced, wherein
- the seal is a tubular seal made of an elastic material;
- the seal comprises at least two tube sections fixed to each other;
- folds of the at least two tube sections have opposing twisting angles;
- one end of the seal is fastened to the outer element and the other end is fastened to the inner element; and
- the seal is arranged to twist by a torque proportional to the phase difference between the inner and outer elements.

10. A measuring device as claimed in claim 9, wherein the measuring device is arranged to determine the torque of the seal on the basis of the phase difference between the inner and outer elements as a linear function;
- the measuring device is arranged to determine the fluid property on the basis of the torque of the seal.

11. A measuring device as claimed in claim 9, wherein at least one tube section of the seal is inside at least one other tube section so that the tube section which is inside and the end of which forms one end of the seal is fastened to the inner element and the other end of the seal is fastened to the outer element.

12. A measuring device as claimed in claim 9, wherein the ends of the seal are arranged so that they do not twist with respect to each other.

13. A measuring method, wherein a property of a fluid is measured on the basis of a phase difference between an outer element coaxially arranged with and configured to surround an inner element, with the inner and outer elements being configured to share a common axis and to rotate in the same direction, the phase difference being produced by the torque between the inner and outer elements the fluid has caused, comprising
- producing by a seal, which is a tubular seal made of an elastic material and comprising at least two tube sections fixed to each other, a torque twisting in the opposite direction than the torque caused by the fluid between the inner and outer elements and being proportional to the phase difference between the inner and outer elements; wherein
- each tube section comprises at least one fold;
- the folds of the at least two tube sections have opposing twisting angles;
- one end of the seal is fastened to the outer element and the other end is fastened to the inner element;
- the phase difference between the inner and outer elements is measured; and
- the fluid property is determined on the basis of the phase difference.

14. A method as claimed in claim 13, furthering comprising determining the torque of the seal on the basis of the phase difference between the inner and outer elements by a linear function, and determining the fluid property on the basis of the determined torque of the seal.

15. A seal manufacturing method, wherein the seal is intended for sealing an axis pair of a measuring device, the axis pair including an outer element coaxially arranged with and configured to surround an inner element, with the inner and outer elements being configured to share a common axis and to rotate in the same direction, and a phase difference between the inner and outer elements is arranged to remain within predetermined limits, comprising
- making a tubular seal of an elastic material;
- providing the seal with at least two tube sections;
- providing each tube section with at least one fold, a twisting angle of which differs from the direction of the longitudinal axis of the tubular seal;
- providing the at least two tube sections with folds having opposing twisting angles to make the torque caused by the twisting of the seal during the measurement proportional to the phase difference between the inner and outer elements;
- providing the seal ends with fastening parts, by which the seal can be fastened to the inner and outer elements in such a manner that one end of the seal is fastened to the outer element and the other end is fastened to the inner element.

16. A method as claimed in claim 15, further comprising manufacturing the tube sections separately and fixing the tube sections to each other to form a continuous seal.

17. A method as claimed in claim 15, further comprising placing at least one tube section of the seal inside at least one other tube section, whereby the tube section which is inside and the end of which forms one end of the seal can be fastened to the inner element and the other end of the seal can be fastened to the outer element.

* * * * *